United States Patent
Jiang et al.

(10) Patent No.: US 8,894,570 B2
(45) Date of Patent: Nov. 25, 2014

(54) VIDEO LARYNGOSCOPE

(75) Inventors: Wenqiang Jiang, Suzhon (CN); Li Ding, Shanghai (CN)

(73) Assignee: Li Ding, Shanghai (CN)

( * ) Notice: Subject to any disclaimer, the term of this patent is extended or adjusted under 35 U.S.C. 154(b) by 301 days.

(21) Appl. No.: 13/138,112

(22) PCT Filed: Dec. 31, 2009

(86) PCT No.: PCT/CN2009/076326
§ 371 (c)(1),
(2), (4) Date: Jul. 6, 2011

(87) PCT Pub. No.: WO2010/083717
PCT Pub. Date: Jul. 29, 2010

(65) Prior Publication Data
US 2011/0270038 A1 Nov. 3, 2011

(30) Foreign Application Priority Data

Jan. 22, 2009 (CN) .................... 2009 2 0067327 U
Aug. 24, 2009 (CN) .................... 2009 1 0194495

(51) Int. Cl.
*A61B 1/267* (2006.01)
*A61B 1/00* (2006.01)
*A61B 1/06* (2006.01)

(52) U.S. Cl.
CPC . *A61B 1/267* (2013.01); *A61B 1/06* (2013.01); *A61B 1/00073* (2013.01); *A61B 1/00052* (2013.01)
USPC .......................................... 600/194

(58) Field of Classification Search
USPC .................. 600/185, 188, 190, 194
See application file for complete search history.

(56) References Cited

U.S. PATENT DOCUMENTS

| 5,919,183 | A | * | 7/1999 | Field .......................... 604/530 |
| 6,146,402 | A | | 11/2000 | Munoz ......................... 606/194 |
| 2007/0106121 | A1 | * | 5/2007 | Yokota et al. ................. 600/188 |
| 2008/0294010 | A1 | * | 11/2008 | Cooper ........................ 600/199 |

FOREIGN PATENT DOCUMENTS

| CN | 2301219 Y | 12/1998 |
| CN | 200951074 Y | 9/2007 |
| CN | 201022698 Y | 2/2008 |

OTHER PUBLICATIONS

International Search Report of PCY/CN2009/076326 dated Apr. 15, 2010 by Qiwei Zheng of the State Intellectual Property Office in China.

* cited by examiner

*Primary Examiner* — Christian Sevilla

(57) ABSTRACT

A video laryngoscope has a handle and a groove on one side of the handle. The groove is used for guiding a guide wire when the larynogoscope is placed in a patient's mouth. A video camera located near the end of the handle is used to view the area around the glottis. When the guide wire is properly positioned near the glottis, the upper part of the guide wire is disengaged from the groove so as to allow an endotracheal tube to be slipped over the guide wire and to be inserted into part of the trachea through the glottis. When the tube is properly inserted for intubation, the guide wire is removed from the tube. An illuminating light source such as an LED lamp can be installed at the end of the handle to provide illumination for the video camera.

14 Claims, 5 Drawing Sheets

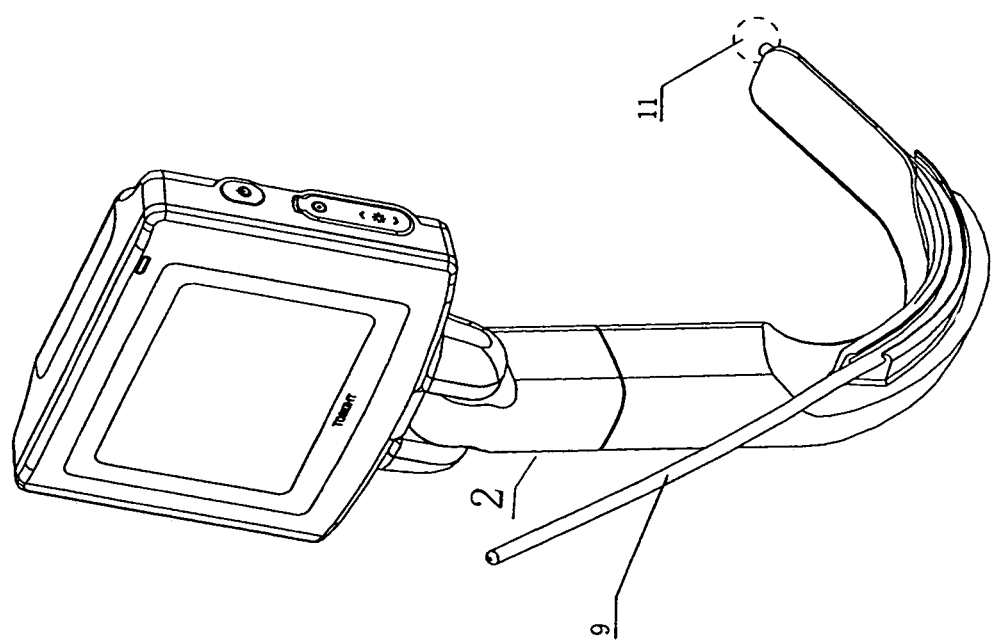

VIDEO LARYNGOSCOPE

CROSS REFERENCE TO RELATED APPLICATION

This application claims priority from CN 2009 20067327.5 filed Jan. 22, 2009, CN 2009 10194495.5 filed Aug. 24, 2009, and PCT/CN2009/076326 filed Dec. 31, 2009.

TECHNICAL FIELD

The invention relates to a laryngoscope for trachea intubation in clinical anesthesia and emergency rescue occasions, particularly an electronic video laryngoscope with a trachea cannula guide groove for difficult intubation. The specially-designed trachea guide wire and guide groove structure apply to all difficult intubation occasions of trachea intubation with laryngoscope.

TECHNICAL BACKGROUND

Tracheal intubation is needed in clinical emergency rescue or general anesthesia occasions. However, the patient is normally in suffocation or non-breathing state at the moment. Although the electronic video laryngoscope improved the intubation exposure conditions, there are still intubation difficulties or throat injuries, especially for patients with high larynx, the rate of intubation difficulties or throat injuries is rather high.

By means of direct observation of video laryngoscope with trachea cannula guide groove, a thinner trachea guide wire can be easily inserted into the glottis via the trachea cannula guide groove. Then the endotracheal tube can be guided in by means of a trachea guide wire to complete the intubation process. A large number of clinical validations showed that this method not only improves the intubation exposing conditions but also avoids injury to the laryngeal part of the pharynx. Thus, it solves all difficulties that trachea intubation may face.

In order to achieve the above methods, a video laryngoscope with a trachea cannula guide groove and the function of guiding trachea intubation guide wire must be specially designed. Furthermore, the structure of the trachea cannula guide groove for guiding trachea intubation guide wire must be specially designed.

SUMMARY OF INVENTION

The purpose of the invention is to solve a technical problem, i.e: to provide a video laryngoscope with a trachea cannula guide groove which applies to all difficult occasions of tracheal intubation.

The invention also provides a method that is capable of guiding the trachea guide wire to any glottis position exposed by any electronic video laryngoscope in any difficult situations, and then guiding the endotracheal tube to complete tracheal intubation under difficult occasions.

To solve the first technical problem, the invention provides a video laryngoscope with a trachea cannula guide groove for difficult intubation, including handle, video camera and trachea cannula guide groove laryngoscope lens, handle clamping sleeve and liquid crystal display (LCD). The trachea guide groove is an arc-shape trachea cannula guide groove on the laryngoscope lens with handle. A trachea guide wire can be put in the trachea cannula guide groove. After the endotracheal tube is inserted with the trachea guide wire, the endotracheal tube can be guided to the glottis position. The trachea guide wire can be separated with guide groove via a breach on the side of the guide groove.

The trachea cannula guide groove on laryngoscope lens is integrated or separated with laryngoscope lens. The separated trachea cannula guide groove can be connected to a laryngoscope lens by ultrasonic welding or adhesive cement.

The trachea cannula guide groove on the laryngoscope lens is located at the side of or below the video camera.

The cross-section of the trachea cannula guide groove is of "kidney-shape". The two semi-circular radius R are greater than that of the trachea guide wire.

The trachea cannula guide groove is a cannula with a slot, or a clamp with a clip and hook. The cannula with a slot can accommodate the trachea guide wire; the clamp with a clip and/or hook can hold a trachea guide wire when it enters the trachea and can separate them.

The handle clamping sleeve and liquid crystal display are connected via damper rotation joint.

The laryngoscope lens and liquid crystal display with handle, video camera and trachea cannula guide groove are removable and connected to the handle clamping sleeve through sleeve slip. After clamping, the electrical connections between them are via conductive contacts.

At the front of the laryngoscope lens with handle, the video camera and the trachea cannula guide groove are the lighting lamp, the video camera and the heat defogging circuit.

The laryngoscope lens with handle and trachea cannula guide groove comprises a sealed laryngoscope lens casing and casing cover. The lighting lamp at the front is sealed with the casing. Inside the casing are a camera, an image signal processing circuit and heat defogging circuit. At the front of laryngoscope lens are a heating element and a temperature sensor. After processing the camera input signals, the image signal processing circuit sends the signals to LCD via conductive contacts and the handle clamping sleeve on the laryngoscope lens.

In order to solve the second technical problem, the invention provides a guide trachea intubation for difficult intubation. See the following steps:

Step 1: Insert the video laryngoscope lens with the trachea cannula guide groove into the oral cavity and expose the glottis;
Step 2: Under the monitoring of video laryngoscope, insert the trachea guide wire into the glottis via the trachea cannula guide groove;
Step 3: Disassemble the trachea guide wire with the guide groove through the slot of the trachea cannula guide groove;
Step 4: Put the trachea guide wire into the endotracheal tube and insert the endotracheal tube into the patient's trachea via the trachea guide wire and the glottis under the surveillance of the video laryngoscope;
Step 5: Pull out the trachea guide wire from the endotracheal tube under the surveillance of a video laryngoscope;
Step 6: Remove the video laryngoscope lens with the trachea cannula guide groove from the throat to complete the whole process of trachea intubation.

FEATURES OF THE INVENTION

1) The electronic video laryngoscope with a trachea cannula guide groove can be used through the observation on the color LCD mounted on the handle. The trachea guide wire can be inserted into any glottis position exposed by the video laryngoscope. The endotracheal tube can then be guided in to perform difficult intubation.

2) The trachea guide wire is inserted first by means of the trachea cannula guide groove on the video laryngoscope; then, the endotracheal tube is guided in by means of the trachea guide wire. This method solves the problem that the general video laryngoscope can only expose the glottis under difficult intubation situations but difficult to insert the trachea cannula. Thus, it avoids or reduces the injury to the larynx and trachea during intubation.

3) The trachea cannula guide groove is in an approximate arc curve. It is convenient to lead the guide wire into the exposed glottis;

4) The cross-section of the trachea cannula guide groove is of a "kidney-shape". The two semi-circular radius R at both ends are greater than that of the trachea guide wire. This can make the guide wire run easily in the trachea cannula guide groove and will not slip out easily.

5) The opening slot provided on one side of the "kidney-shape" can let the trachea guide wire be easily removed from the trachea cannula guide groove after it is inserted into the glottis.

6) The laryngoscope lens handle and LCD parts can be easily dismantled so that the laryngoscope lens can be immersed for disinfection for repeated use;

7) The video laryngoscopy with a trachea cannula guide groove not only can improve the intubation exposing conditions but also reduce the injury to the larynx. It solves the problems of trachea cannula under difficult intubation with laryngoscopy.

BRIEF DESCRIPTION OF THE DRAWINGS

FIG. 5 is a trachea guide wire being inserted into the glottis via the trachea cannula guide groove;

| Legends: | |
|---|---|
| 1 - laryngoscope lens; | |
| 101 - laryngoscope casing; | 102 - electrical contacts; |
| 103 - Ball-bearing retainer; | 104 - video camera; |
| 105 - LED lamp; | 106 - temperature sensor; |
| 107 - heating element; | 108 - laryngoscope lens transparent front; |
| 109 - trachea cannula guide groove; | |
| 2 - handle clamping sleeve; | |
| 201 - spring pin contacts; | 202 - metal retainer sleeve; |
| 3 - damping rotating joint; | 4 - LCD; |
| 5 - battery life indicator; | 6 - operation indicator; |
| 7 - charging socket; | 8 - operation switch; |
| 9 - trachea guide wire; | 10 - endotracheal tube; |
| 11 - glottis. | |

DETAILED DESCRIPTION

See the figures below for further illustration on the invention.

Figure 1:
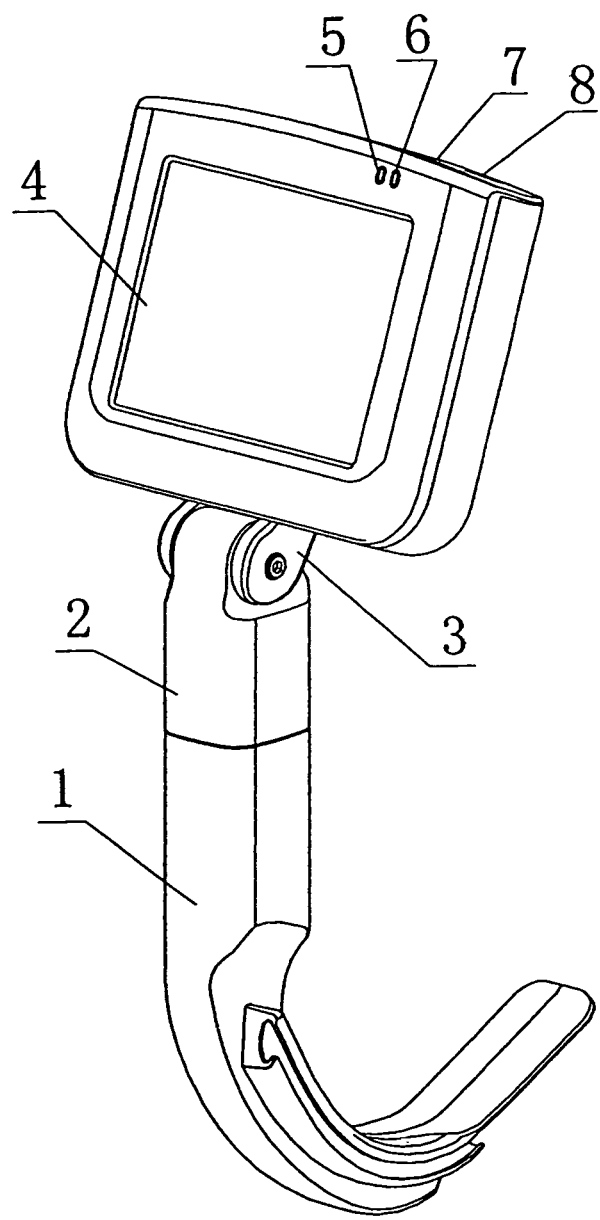
FIG. 1 is a structural diagram of this new, practical and integrated utility model.
Figure 2:
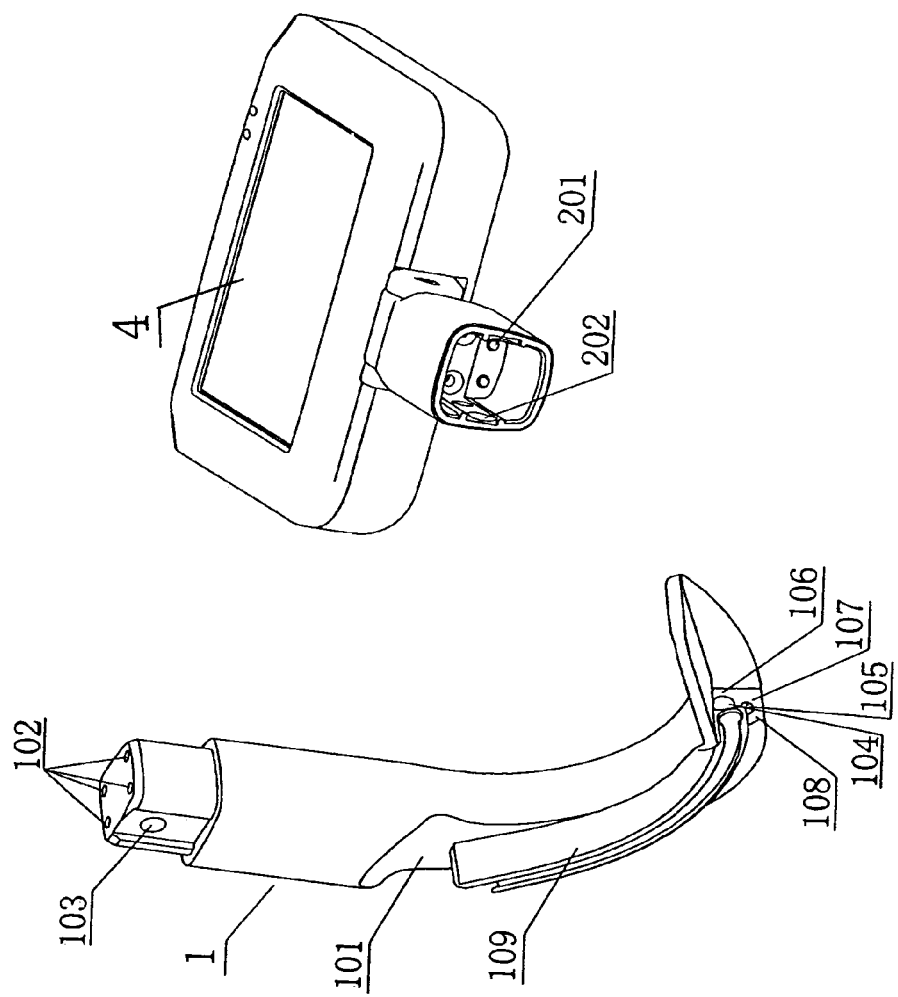
FIG. 2 is a decomposed diagram of FIG. 1.
Figure 3:
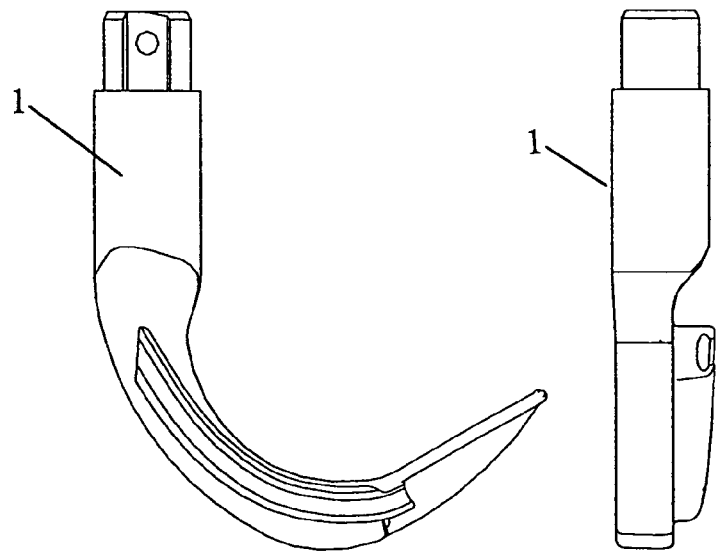
FIG. 3 is a structural diagram of a trachea cannula guide groove (shown in FIG. 1) on the laryngoscope.

As shown in FIG. 1, FIG. 2 and FIG. 3, the invention provides a video laryngoscope with a trachea cannula guide groove for difficult intubation including a handle, a video camera and a trachea cannula guide groove laryngoscope lens 1, handle clamping sleeve 2 and liquid crystal display 4. The trachea guide groove is an arc-shape trachea cannula guide groove 109 on the laryngoscope lens 1 with handle. A trachea guide wire 9 can be put in the trachea cannula guide groove 109. After the endotracheal tube 10 is inserted with the trachea guide wire 9, the endotracheal tube 10 can be guided into the glottis 11. The trachea guide wire 9 can be separated with guide groove 109 via a breach on the side of the guide groove.

The trachea cannula guide groove 109 on the laryngoscope lens is integrated or separated with laryngoscope lens 1. The separated trachea cannula guide groove 109 can be connected to a laryngoscope lens 1 by ultrasonic welding or adhesive cement.

Figure 4:
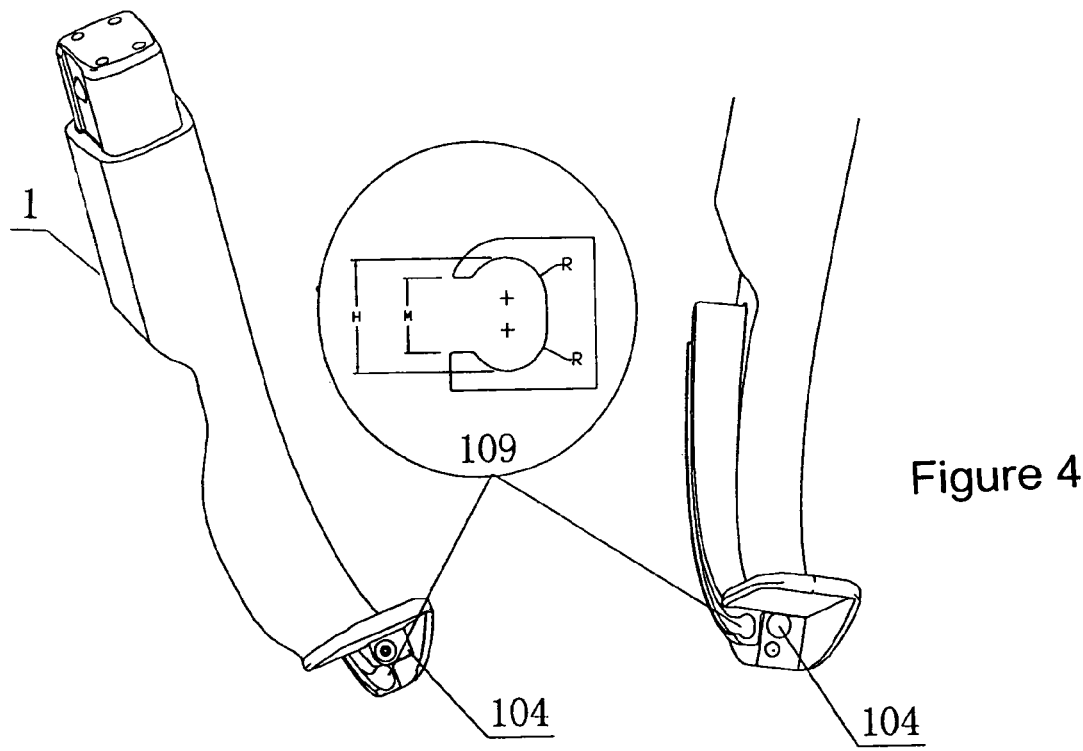
FIG. 4 is a relative position of the trachea cannula guide groove and camera (shown in FIG. 1) and the cross-section diagram of the guide groove.

As shown in FIG. 4, the trachea cannula guide groove 109 on laryngoscope lens 1 is located at the side of or below the video camera 104.

The cross-section of the trachea cannula guide groove 109 is of "kidney-shape". The two semi-circular radius R are greater than that of the trachea guide wire 9. An opening slot is at the front end of the trachea cannula guide groove 109 in front of the laryngoscope lens 1. The opening width of the opening slot is greater than the diameter D of trachea guide wire 401.

The trachea cannula guide groove is a cannula with slot, or a clamp with clip and hook. The cannula with slot can accommodate the trachea guide wire 9; The clamp with clip and/or hook can hold the trachea guide wire 9 when it enters the trachea and can separate them.

The handle clamping sleeve 2 and liquid crystal display 4 are connected via the damper rotation joint 3. The laryngoscope lens 1 and liquid crystal display 4 with handle, video camera and trachea cannula guide groove are removable and connected to the handle clamping sleeve 2 via a sleeve slip. The laryngoscope lens 3 with handle, video camera and trachea cannula guide groove can be separately immersed for disinfection after dismantling; When the handle clamping sleeve 2 is put on the laryngoscope lens 1 with handle, the ball-bearing retainer 103 on laryngoscope lens 1 is connected to a metal retainer sleeve 202 in the handle clamping sleeve 2. After connection, the laryngoscope lens 1 with handle, video camera and trachea cannula guide groove is fixed to LCD 4 on sleeve 2. Six conductive contacts 102 on laryngoscope lens 1 are connected to six corresponding spring pin contacts 201 in handle clamping sleeve 2.

At the front of the laryngoscope lens 1 with handle, video camera and trachea cannula guide groove are a lighting lamp 105, a video camera 104 and a heat defogging circuit. At the side is the trachea cannula guide groove 109. Handle clamping sleeve 2 is connected to LCD 4 via damping rotating joint 3. When the installation is completed, LCD 4 can be rotated via damping rotating joint 3 to adapt various clinical operations; the in-between of LCD 4 and the laryngoscope lens handle can be fixed at any degree within the rotation range for easy observation.

The laryngoscope lens 1 with handle, video camera and trachea cannula guide groove comprises a laryngoscope lens casing and casing sealing cover. Outside the casing is the trachea cannula guide groove 109. An LED lamp 105 at the front 108 is sealed with casing 101. Video camera 104, image and signal processing circuit and heating defogging circuit are installed in the casing 101. At the front end 108 of the laryngoscope lens are a temperature sensor 106 and a heating element 107. After processing the input signal from video camera 104, the image and signal processing circuit sends it to LCD 4 via conductive contacts 102 on the laryngoscope lens and the handle clamping sleeve 2.

At the side of LCD 4 are operation switch 8 and charging socket 7. At the top are the operation indicator 6 and the battery life indicator 5.

Connect disinfected laryngoscope lens 1 with handle, video camera and trachea cannula guide groove to handle clamping sleeve 2. Press operation switch 8, then LCD 4 and lighting LED 105 will be on.

Figure 7:
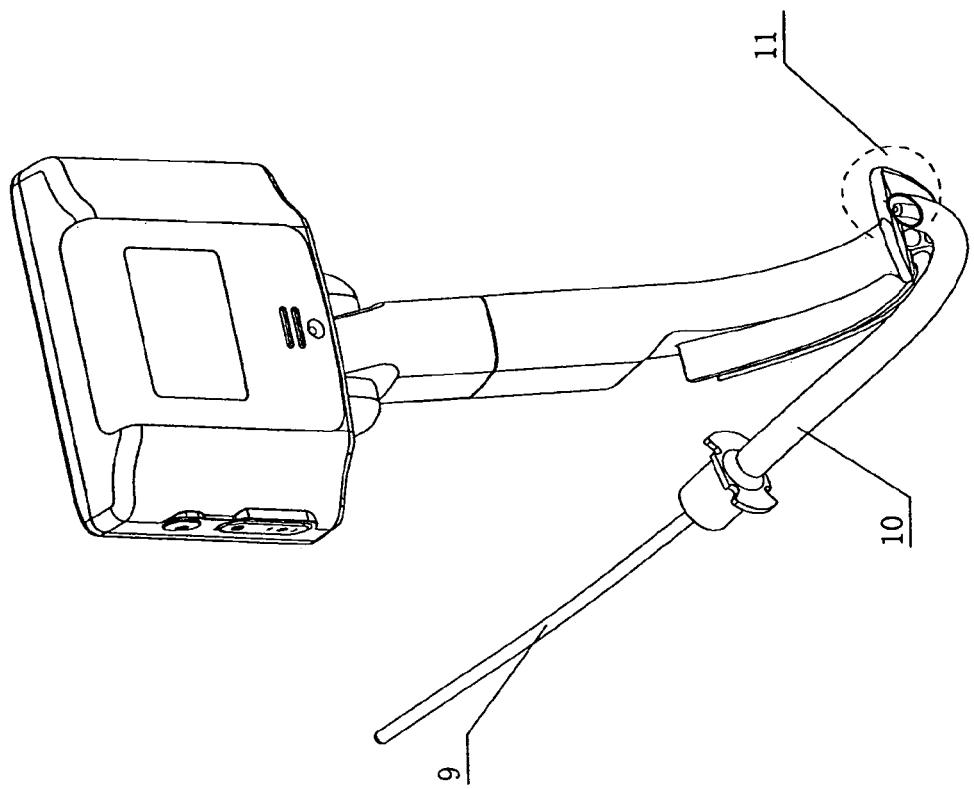
FIG. 7 shows an endotracheal tube being inserted into the glottis via the trachea guide wire.
Figure 6:
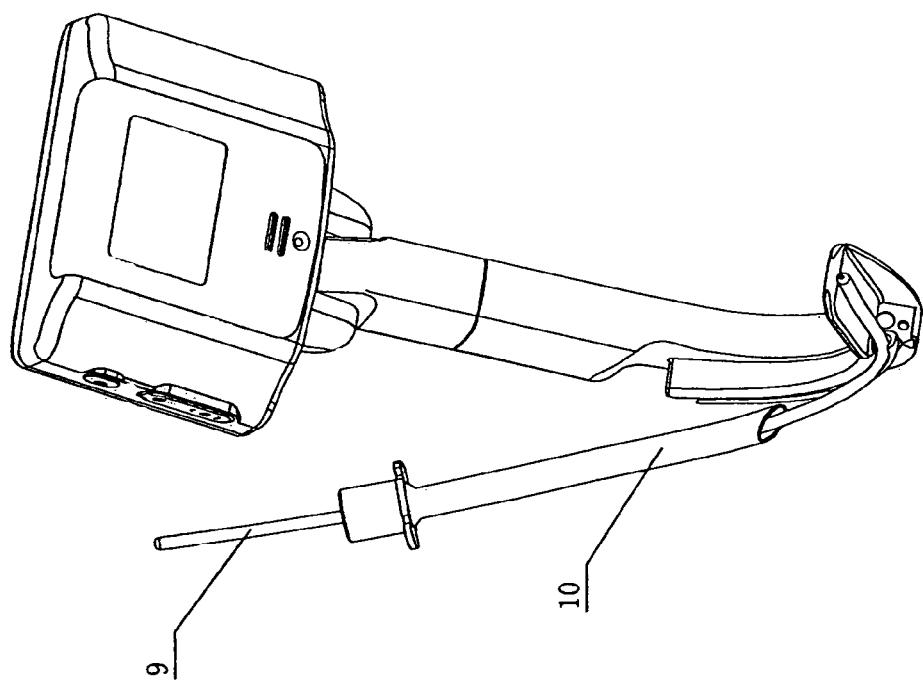
FIG. 6 shows a trachea guide wire being inserted into the endotracheal tube and separated with the trachea cannula guide groove.

As shown in FIGS. 5, 6, and 7, the laryngoscope lens 1 is inserted into the oral cavity of the patient. The signal processing circuit in the image sensor video camera 104 and laryngoscope casing 101 transforms the image from the patient's trachea into video signal and displays it on LCD 4 monitor. The operator can observe the exposed glottis 11 via LCD 4 installed on the handle. First, insert the trachea guide wire 9 into the glottis via trachea cannula guide groove 109; then, retreat the trachea guide wire 9 from the trachea cannula guide groove 109 via the side slot of the trachea cannula guide groove 109; put the trachea guide wire 9 into the endotracheal tube 10; insert the endotracheal tube 10 to the glottis along the trachea guide wire 9; pull back the trachea guide wire 9. Finally, retreat from video laryngoscope lens 1 and complete the whole trachea intubation.

What is claimed is:

1. A laryngoscope, comprising:
a handle having a first handle end and a second handle end;
a camera disposed on the second handle end, the camera configured to view an area around a glottis;
a groove located on one side of the handle, the groove comprising a groove end adjacent to the camera;
a guide wire; and
a tube dimensioned for slipping over the guide wire, the groove dimensioned for guiding the guide wire through the groove to reach the groove end, the guide wire comprising a first wire end and an opposing second wire end, the second wire end arranged to reach the groove end while the guide wire is engaged in the groove, the groove also dimensioned to allow the guide wire to disengage from the groove so as to allow the tube having a tube end to slip over the guide wire to reach the second wire end while the groove end remains adjacent to the second wire end to allow the camera to view the area around the glottis wherein the groove comprises a breach to allow the guide wire to disengage from the groove and the groove has an elongated cross section, the cross section having a wider side and a narrower side, wherein the wider side having a shape defined by two semi-circles separated by a substantially straight middle section and the shorter side has an opening for providing the breach, and wherein the semi-circles are dimensioned to guide the guide wire.

2. The laryngoscope according to claim 1, wherein the camera comprises a video camera, and the tube end is dimensioned for insertion into a trachea through a glottis, said laryngoscope further comprising
a light source arranged to provide illumination at least when the video camera is used to view an area around the glottis.

3. The laryngoscope according to claim 1, further comprising:
an image display arranged to display images acquired by the camera.

4. The laryngoscope according to claim 3, wherein the image display is mounted on the first handle end.

5. A method comprising:
providing a groove on a laryngoscope, the laryngoscope comprising a guide wire, a tube and a handle, the handle having a first handle end and a second handle end, the second handle end arranged to be placed near a glottis, the tube dimensioned for slipping over the guide wire, the groove located on one side of the handle, the groove comprising a groove end adjacent to the second handle end, and
the groove dimensioned to guide the guide wire through the groove to reach the groove end, the guide wire comprising a first wire end and an opposing second wire end, the second wire end arranged to reach the groove end while the guide wire is engaged in the groove, the groove also dimensioned to allow the guide wire to disengage from the groove so as to allow the tube having a tube end to slip over the guide wire to reach the second wire end while the groove end remains adjacent to the second wire end wherein the groove comprises a breach to allow the guide wire to disengage from the groove and the groove has an elongated cross section, the cross section having a wider side and a narrower side, wherein the wider side having a shape defined by two semi-circles separated by a substantially straight middle section and the shorter side has an opening for providing the breach, and wherein the semi-circles are dimensioned to guide the guide wire.

6. The method according to claim 5, further comprising:
providing a video camera at the second handle end, the video camera arranged for viewing an area around the glottis at least when the second wire end of the guide wire reaches the groove end.

7. The method according to claim 6, further comprising:
providing illumination to the area around the glottis at least when the video camera is arranged to view the area.

8. The method according to claim 6, further comprising:
providing an image display on the first handle end, the image display arranged to display images acquired by the video camera.

9. A method of operating a laryngoscope when inserting a tube into a trachea through a glottis over a guide wire, the laryngoscope comprising a handle comprising a handle end and a video camera at the handle end, said method comprising:
placing the handle end near an oral cavity in a mouth to expose the glottis, the handle comprising a groove located on one side of the handle, the groove comprising a groove end located near the handle end;
operating the video camera for viewing an area around the glottis;
inserting the guide wire having a first wire end and an opposing second wire end into the groove until the second wire end at least reaches the groove end and the glottis while the video camera is viewing the area around the glottis, wherein the groove is dimensioned to guide the wire for said inserting so that the guide wire is engaged with the groove in said inserting;
disengaging the first wire end of the guide wire from the groove; and
slipping the tube over the guide wire from the first wire end until the tube end reaches at least the second wire end, wherein the tube is dimensioned for said slipping wherein the groove comprises a breach for said disengaging and the groove has an elongated cross section, the cross section having a wider side and a narrower side, wherein the wider side having a shape defined by two semi-circles separated by a substantially straight middle section and the shorter side has an opening for providing the breach, and wherein the semi-circles are dimensioned to guide the guide wire for said inserting.

10. The method according to claim 9, further comprising: moving the tube over the guide wire toward the glottis until the tube end is inserted into at least part of the trachea through the glottis.

11. The method according to claim 10, further comprising: removing the guide wire from the tube.

12. The method according to claim 11, further comprising: removing the laryngoscope from the mouth.

13. The method according to claim 9, further comprising: removing the guide wire from the tube while the video camera is viewing the area around the glottis.

14. The method according to claim 13, further comprising: removing the laryngoscope from the mouth.

* * * * *